United States Patent [19]
Folkers et al.

[11] Patent Number: 4,885,167
[45] Date of Patent: Dec. 5, 1989

[54] RESTORATION OF IMPAIRED CARDIAC FUNCTION OF PATIENTS WITH DIVERSE MUSCULAR DYSTROPHIES BY THERAPY WITH COENZYME Q10

[75] Inventors: Karl Folkers, Austin, Tex.; Janusz Wolaniuk, Indianapolis, Ind.

[73] Assignee: Board of Regents, The University of Texas System, Austin, Tex.

[21] Appl. No.: 155,891

[22] Filed: Feb. 16, 1988

Related U.S. Application Data

[63] Continuation-in-part of Ser. No. 725,059, Apr. 19, 1985, abandoned.

[51] Int. Cl.$^4$ ............................................. A61K 37/48
[52] U.S. Cl. .................................... 424/94.1; 514/907
[58] Field of Search ...................... 424/94.1; 514/907

[56] References Cited

U.S. PATENT DOCUMENTS

| | | | |
|---|---|---|---|
| 4,068,003 | 1/1978 | Miyata | 424/94.1 |
| 4,156,718 | 5/1979 | Blizrakov | 424/94.1 |
| 4,491,594 | 1/1985 | Ogawa et al. | 424/94.1 |

OTHER PUBLICATIONS

Folkers et al., "Evidence for a Deficiency of Coenzyme $Q_{10}$ in Human Heart Disease", International Journal for Vitamin Research, 1970, pp. 380–390.
Ganong, W. F., "The Heart as a Pump", In: Review of Medical Physiology, Los Altos, Lange Medical Publication, pp. 441–451 (1981).
Baker et al., "Use of Electrical Impedance to Measure Cardiac Function In Studies of $CoQ_{10}$", Elsevier/-North–Holland Biomedical Press, 1981, pp. 193–206.
Vadhanavikit et al., "Micro–Analysis for Coenzyme $Q_{10}$ in Endomyocardial Biopsies of Cardiac Patients and Data on Bovine and Canine Hearts", Biochemical and Biophysical Resrch. Comm. Vo. 123, No. 3, 1984 pp. 1165–1169.
Mortensen et al., "Deficiency of Coenzyme $Q_{10}$ in Myocardial Failure," Drugs Exptl. Clin. Res. (7), 1984, pp. 497–502.
Folkers et al., "Biochemical Rationale and The Cardiac Response of Patients With Muscle Disease To Therapy With Coenzyme $Q_{10}$", Proc. Natl. Acad. Sci. USA, vol. 82, Jul. 1985, pp. 4513–4516.
DePierre et al., "Enzyme Topology of Intracellular Membranes", Ann. Rev. Biochem., 1977, pp. 201–262.
Crane et al., "Isolation of a Quinone From Beef Heart Mitochondria", Biochem. Biophys. Acta, vol. 25, 1957, pp. 220–221.
Saviotti et al., "Electrocardiography in Duchenne Muscular Dystrophy", G. Neuropsichiatr Eta Evol., 1984, 4/Suppl. 1 (67–69), p. 337.
Venco et al., "The Heart in Progressive Muscular Dystrophy", G. Neuropsychiatr Eta Evol., 1984, 4/Suppl. 1 (61–66), p. 341.
Carafoli et al., "Molecular Aspects of Medicine" (1980) Molec. Aspects of Med., V3, pp. 295–429.
Sunamori et al., "Clinical Application of Coenzymer Q To Coronary Bypass Graft Surgery" (1984) Biomed. and Clin, Aspects of Coenzyme Q, ed Folkers et al., V4, pp. 333–342.
Michelson et al., "Dystrophia Muscularis: A Hereditary Primary Myopathy In the House Mouse", 1955) Proc. Nat'l. Acad. Sci., V 41, pp. 1079–1084.
West, "Hereditary Mouse Muscular Dystrophy With Particular Emphasis on Pathogenesis and Attempts At Theraphy", (1966) Annals. N.Y. Accas. Of Sciences, V 138, pp. 4–13.
Welsh et al., "Cardiac Findings in 73 Patients with Muscular Dystrophy", (1963) Arch. Int. Med., V 112, pp. 97–104.
Durnin et al., "The Electrocardiogram in Pseudohypertrophic or Duchenne's Muscular Dystrophy (Type IIIa)", (1960) J. Iowa Med. Soc., V 59, pp. 113–115.
Morgan–Hughes, "Disorders of Mitochondrial Metabolism Some Clinical and Biochemical Mechanisms", (1983), Advanced Med., V 19 ed by Saunders, pp. 243–260.
Farley et al., "Response Of Genetically Dystrophic Mice to Therapy With Hexahydrocoenzyme $Q_4$", (196) Biochem. and Biophys. Res. Comm. V 24, pp. 299–303.
Nilsson et al., "Biosynthesis and Levels of Coenzyme Q in Genetically Dystrophic Mice", (1968) Arch. Biochem. and Biophys. V 133, pp. 422–426.
Lenaz et al., "Organic Structural Specificity and Sites of Coenzyme Q in Succinoxidase and DPNH–Oxidase Systems", (1968) Arch. Biochem. and Biophys., V 123 pp. 539–550.

(List continued on next page.)

Primary Examiner—John W. Rollins
Attorney, Agent, or Firm—Arnold, White & Durkee

[57] ABSTRACT

The present invention relates to the use of Coenzyme Q in the treatment of slow muscle degeneration, commonly known to those of skill in the art so a dystrophy or atrophy, and the accompanying cardiac complications typically identified in such patients. Administration of Coenzyme Q, and particularly the analog Coenzyme $Q_{10}$ ($CoQ_{10}$) to humans increases the pumping of blood by the heart, and thereby increases tissue oxygeneration throughout the body. The net physiological effect halts the progression of muscle deterioration and improves cardiac function. An overall improvement in the quality of life for these human subjects is also observed, said patients reportedly experiencing less fatigue.

A method for treating human patients with progressive muscular dystrophies or the neurogenic atrophies with Coenzyme $Q_{10}$ ($CoQ_{10}$) specifically disclosed. The method is similarly effective for the treatment of any form of muscle degeneration or cardiac muscular dysfunction independently.

1 Claim, No Drawings

OTHER PUBLICATIONS

Scholler et al., "Therapeutic Activity of Coenzyme Q for Reproduction", (1968) International J. for Vit. Res., V 38, pp. 362–368.

Littarru et al., "Deficiency of Coenzyme $Q_9$ in Mice Having Hereditary Muscular Dystrophy", (1970) Biochem. and Biophys. Res. Comm., V 41, pp. 1306–1313.

Danowski et al., "Tabulation of Findings in the Muscular Dystrophies and in Myotonia Dystrophica", (1971) (I) Arch. of Physical Med. and Rehab., V 52, pp. 193–200.

Sovik et al., "Coenzyme Q in Duchenne Muscular Dystrophy", (1971), Acta Pediat. Scand., V 60, pp. 428–432.

Danowski et al., "Hexahydrocoenzyme $Q_4$ in Pseudohypertrophic Muscular Dystrophy", (1971) II J. Pharmacent. Sci., V 60, pp. 640–642.

Zellweger et al., "The Diagnostic Significance of Serum Enzymes and Electrocardiogram in Various Muscular Dystrophies", (1972) Internat. J. Vit. Nutr. res., V 42, pp. 139–163.

Folkers et al., "Survey and New Clinical Studies on Coenzyme Q in Human Muscular Dystrophy", (1972) Internat. J. Vit. Nutr. Res., V 42, pp. 139–163.

Griggs (1974) Circal. Res., V 34 and 35, pp. II–145–II–150.

Folkers et al., "Effect of Coenzyme Q on Serum Levels of Creatine Phosphokinase in Preclinical Muscular Dystrophy", (1974) Circal. Res., V 34 and 35, pp. II–145–II–150.

Kuhn et al., "Early Myocardial Disease and Cramping Myalgia in Becker-Type Muscular Dystrophy: A Kindered", (1979) Neurology, V 29, pp. 1144–1149.

Reeves et al., "Echocardiohgraphic Evaluation of Cardiac Abnormalities in Duchene's Dystrophy and Myotonic Muscular Dystrophy", (1980) Arch. Neurol., V 37, pp. 273–277.

Hopkins et al., "Emery-Dreifuss Humeroperoneal Muscular Dystrophy: An X-linked Myopathy with Unusual Contractures and Bradycardia", Annals of Neurol. (1981), V 10, pp. 230–237.

Kishi et al., "Estimation of Plasma Levels of Coenzyme $Q_{10}$ and Relationship to Oral Dosage", (1981) Biomed. and Clin, Aspects of Coenzyme Q, V 3, eds Folders et al., pp. 67–78.

Couch et al., "Coenzyme Q In Therapy of Limb-Girdle Muscular Dystrophy", (1981) ibid., pp. 257–266.

Folkers et al., "New Progress on the Biomedical and Clinical Research on Coenzyme Q", (1981) ibid., pp. 399–412.

Goldberg et al., "Serial Two-Dimensional Echocardiography in Duchenne Muscular Dystrophy", (1982) Neurology, V 32 pp. 1101–1105.

Hawley et al., "Families With Myotonic Dystrophy With and Without Cardiac Involvement", (1983) Arch. Int. Med., V 143, pp. 2134–2136.

Bender, "Diagnosis: Muscular Dystrophy", (1984) Hospital Med. Hanuary, pp. 95–125.

Morgan-Hughes et al., "Mitochondrial Myopathies Results of Exploratory Therapeutic Trials", (1984) Biomed and Clin. Aspects of Coenzyme Q, Elsevier Science Pub., V 4, pp. 417–424.

Ho et al., "Genetic Dystrophy in Mice, A Possible Coenzyme Q Dependency State", (1975) Abstract of Presented Paper.

Kubicek et al., "Development and Evaluation of an Impedance Cardiac Output System", (1966) Aerospace Med. (Dec. 1966) pp. 1208–1212.

4,885,167

RESTORATION OF IMPAIRED CARDIAC FUNCTION OF PATIENTS WITH DIVERSE MUSCULAR DYSTROPHIES BY THERAPY WITH COENZYME Q10

This application is a continutaion-in-part of application Ser. No. 06/725,059 filed 04/19/85 now abandoned.

THE INVENTION

In January, 1984, (Bender, A. N., *Hosiptal Medicine,* p. 95, January, 1984), stated:

—"The term muscular dystrophy applies to a variable group of disorders—some well defined, and others less well defined—categorized by general features—. All are primarily diagnosed on clinical and genetic grounds, and none of them is treatable at the present time. Accurate diagnosis allows realistic prognosis, effective rehabilitation, and prevention of further cases through genetic counseling."

Griggs, M. D., (Supplement II to Circulation Research, vols. 34 and 35) has stated that:

—"Cardiac disease appears to be the rule rather than the exception in virtually every form of hereditary and acquired skeletal myopathy."

We have made three related discoveries on the administration of coenzyme $Q_{10}$ (vitamin $Q_{10}$) to patients with diverse muscular dystrophies and diverse neurogenic atrophies.

The first discovery was the recognition that, *in spite of the unknown and variable genetic defects, a patient* with a form of muscular dystrophy or *a patient* with a form of neurogenic atrophy, could have the impaired cardiac function be significantly improved by treatment with coenzyme $Q_{10}$ and not improved by treatment with a matching placebo.

The second discovery was the recognition that *all patients* with eight diverse forms of muscular dystrophies and neurogenic atrophies had an increase in their impaired cardiac function by treatment with coenzyme $Q_{10}$. It was almost unbelievable that all patients with such diverse genetic diseases should all respond by this therapy and show a significant increase in the pumping of the blood by their hearts.

The third discovery was the recognition that the impaired cardiac function of many such patients with such diverse disease was not only improved, *but was restored to a normal level of cardiac function.* Such restoration was not even considered. It was thought that a significant increase of the impaired cardiac function to a level below that of the normal range might be possible.

Reduction to practice may be considered as achieved only by the two double blind trials as required by the Food and Drug Administration. The two double blind trials constitute the Reduction to Practice.

These three related discoveries constitute a basis for the Food and Drug Administration to grant an NDA for the clinical use of $CoQ_{10}$ as an orphan drug for months and years of administration and on the basis of complete safety. Since such patients have their genetic defects for a life-time, they may be safely treated with $CoQ_{10}$ for their life-time. A pharmaceutical company may now proceed to market $CoQ_{10}$ as an orphan drug for such patients with an NDA from the F&DA, and with the protection of a use patent.

SUMMARY OF THE APPLICATION

It is known that both cardiac and skeletal muscle contract.

It is known that the contraction of both cardiac and skeletal muscle require energy or "bioenergetics."

Skeletal muscle comprises the great mass of the somatic musculature and has well-developed cross striations, and does not normally contract in the absence of nervous stimulation. Skeletal muscle is generally under voluntary control.

Cardiac muscle does have cross-striations, but is functionally syncytial in character and contracts rhythmically in the absense of external innervation owing to the presence in the myocardium of pacemaker cells that discharge spontaneously. Cardiac muscle contains far larger numbers of elongated mitochondria in close contact with the fibrils than does skeletal muscle.

All forms of dystrophy and atrophy involve genetic defects and these defects vary widely as evidenced by the widely differing symptoms of all of the forms of dystrophy and atrophy or myopathy. These genetic defects have been studied on skeletal muscle because skeletal muscle is available by biopsy in contrast to cardiac muscle which is very difficult to obtain from living patients for ethical reasons. Consequently, little or nothing is known about the differences in genetic defects between cardiac and skeletal muscle although such differences very probably must exist.

Coenzyme $Q_{10}$ is known to provide clinical benefit to patients with congestive heart failure but who have no muscular dystrophy or atrophy or myopathy. There was no basis to predict whether coenzyme $Q_{10}$ would or would not be beneficial to the cardiac dysfunction of patients with these muscular diseases and because of the great diversity of the genetic defects and the great diversity of the clinical symptoms of all these diseases. It appeared probable that any clinical usefulness of administering coenzyme $Q_{10}$ to such patients would be very limited or negative entirely, because of the apparent and diverse genetic defects.

There was no assurance that $CoQ_{10}$ would benefit the cardiac function of dystrophic patients. The first double-blind and open cross-over trial on the oral administration of coenzyme $Q_{10}$ ($CoQ_{10}$) to 12 patients with progressive muscular dystrophies and neurogenic atrophies was conducted. These diseases included the Duchenne, Becker and, limb-girdle dystrophies, myotonic dystrophy, Charcot-Marie tooth disease and Welander disease. Cardiac function was noninvasively and extensively monitored by impedance cardiography. Solely by significant change or no change in stroke volume and cardiac output, all eight patients on blind $CoQ_{10}$ and all four on blind placebo were correctly assigned, $p<0.003$. The monitoring of cardiac function of these 12 patients before the trial revealed degrees of impaired cardiac function ranging from relatively severe to definite to low impairment.

It was discovered that the oral administration of $CoQ_{10}$ gave a substantial and surprising improvement to the impaired cardiac function. This initial double blind trial was only on 12 patients, 8 on blind $CoQ_{10}$ and 4 on blind placebo. It was apparent that even though the cardiac response was significant, $p<0.003$, the two groups of 8 patients and 4 patients, respectively, had too few patients to support biologically the discovery of a positive clinical benefit to cardiac function, when the possibility of such a discovery was so questionable. In a second double blind trial with a total of 15 similar patients, 8 on blind $CoQ_{10}$ and 7 on blind placebo, the discovery was confirmed. All 8 patients on blind $CoQ_{10}$ showed significant cardiac improvement and all 7 on blind placebo were negative. The results of the two trials when combined involved 16 patients on blind $CoQ_{10}$ and 11 patients on blind placebo which is sufficient to document the discovery that $CoQ_{10}$ benefits the cardiac function of dystrophic patients.

Two more discoveries resulted from this research. The second discovery was that $CoQ_{10}$ therapy benefited eight diverse forms of dystrophy and myopathy which is remarkable since these eight dystrophies and myopathies are genetically different and reveal very different clinical symptomatology including early death for the Duchenne dystrophy (up to 20 years of age) and decades of life for other dystrophies such as the Charcot-Marie tooth disease.

The third discovery from the second double blind trial was that the cardiac functions of some of the patients were *restored to a normal range*. A higher dosage and longer treatment could likely increase the cardiac function of even more of the patients.

Consequently, the oral administration of coenzyme $Q_{10}$ to patients with very diverse forms of muscular dystrophy and neurogenic atrophy is very useful, because the resulting improved cardiac function definitely benefits the health through more blood providing more oxygenation throughout the body. Since $CoQ_{10}$ is exceptionally safe, this therapy for patients with such disease may be used as long as required or even for a life-time.

BACKGROUND ON INVENTION STUDIES

Coenzyme Q in Mice with Genetic Dystrophy

Lack of Significance of Animal Dystrophy. There have been many studies involving mice based on the biochemistry of CoQ, but there is no absolute certainty of the relationship of a genetic disease in mice in comparison with that of man. It hardly seems that the genetic defects of mice and man are truly identical, although there can be superficial similarities. One fact proving a difference rather than identity is the existance of $CoQ_9$ in mice and $CoQ_{10}$ in man. Obviously, a promising benefit for mice with a genetic disease does not guarantee a response in man by the same treatment.

An account of studies with CoQ in mice with genetic dystrophy are as follows.

Michelson, A. M., Russel, E. S., and Pinckey, K. H., (*Proc. Natl. Acad. Sci. USA* 41, 1079 (1955)), described a mutation of mice that have a muscular degeneration which resembles progressive muscular dystrophy in humans. West, W. T., Meier, H., and Hoag, W. G., (*Ann. N.Y. Acad. Sci.*, 138, 4 (1966)) considered that dystrophy occurred as a spontaneous autosomal mutation in mice 129/Re which causes muscular weakness, atrophy and a reduced life-span. These mice showed clinical, histological, and physiological similarities to juvenile progressive psudohypertrophic and myotonic dystrophy of man, Erb's dystrophy and, except for the difference in inheritance, the Duchenne dystrophy.

Dystrophic mice which were treated with hexahydrocoenzyme $Q_4$ ($H_6CoQ_4$) improved so that severely dystrophic animals responded and were able to walk using all their legs; (Farley, T. M., Scholler, J., and Folkers, K., *Biochem. Biophys. Res. Commun.* 24, 299 (1966)). A study of the biosynthesis and levels of CoQ in these mice indicated a possible genetic defect in the biosynthesis of p-hydroxybenzoic acid (HBA) from tyrosine rather than a defect between CoQ and HBA or some other defect involving CoQ; (Nilsson, L. G., Farley, T. M., Scholler, J., and Folkers, K., *Arch. Biochem. Biophys.* 123, 422 (1968)). In later studies, these dystrophic mice were treated with $H_6CoQ_4$ when they became unable to use their hind limbs. After two weeks of therapy, their improved condition allowed the use of one or both hind legs, and survival was four times that of control mice; (Scholler, J., Farley, T. M., Folkers, K., *Intern. J. Vitamin Res.* 38, 369 (1968)). This dystrophy was studied as a possible coenzyme Q dependency state; (Ho, L., Folkers, K., *Abstract for 27th Meeting of Southwest Region of American Chemical Society* 88, 38, San Antonio, Tex., December, 1971). Determination of the specific activities of the succinate dehydrogenasecoenzyme $Q_9$ reductase of hearts and hind leg muscles of dystrophic mice revealed a deficiency, $p<0.01$, of the intrinsic $CoQ_9$; (Littarru, G. P., Jones, D., Scholler, J., and Folkers, K., *Biochem. Biophys. Res. Commun.* 41(5), 1306 (1970)). When these dystrophic mice were curatively treated with $CoQ_7$, instead of the intrinsic $CoQ_9$, in the fifth month of their life span of eight months, survival increased to twice that of the control group. $CoQ_7$ was isolated from the mitochondria of the hearts and hind legs of the orally treated mice, substantiating that the $CoQ_7$ was substituting for and correcting the deficiency of $CoQ_9$ in the dystrophy.

Studies with Coenzyme Q on Patients with Genetic Muscle Disease.

Significance of Open Very Limited Trials. The exploratory trials of administering $H_6CoQ_4$ to humans with dystrophy were negative. Couch, J. R. and Folkers, K. (*Biomedical and Clinical Aspects of Coenzyme Q*, Vol 3, K. Folkers and Y. Yamamura, eds., Elsevier/North Holland Biomedical Press, Amsterdam, 257-266, (1981)) administered $CoQ_{10}$ to 2 adults with limb-girdle dystrophy and recorded a transient small improvement in strength, and which appeared to slow deterioration. Such observation is clinically meaningless because the transient small improvement could have been the variation in the symptoms of the disease which are known to occur with the limb-girdle dystrophy and which is not as fatal as Duchenne. It is well known that the symptoms of this dystrophy decrease and improve with time and independent of any treatment.

Folkers, K., Baker, L., Richardson, P. C., Shizukuishi, S., Takemura, K., Drzewoski, J., Lewandowski, J., Ellis, J., (*Biomedical and Clinical Aspects of Coenzyme Q*, Vol. 3, K. Folkers and Y. Yamamura, eds., Elsevier/North Holland Biomedical Press, Amsterdam, 399–412 (1981)) reported the administration of $CoQ_{10}$ to a single adult with a late onset form of muscle disease and observed that the expected deterioration appeared to be retarded. Again, such observation is clinically meaningless, because one does not know what the rate of deterioration would have been in the absence of administration of $CoQ_{10}$.

Again, the patient with this mild dystrophy which is not fatal until late decades is known to have decreased symptoms and increased symptoms over time without any treatment.

Danowski, T. S., Wissinger, H. A., Hohmann, T. C., Gerneth, J. A., Folkers, K., Vester, J. W., and Fisher, E. R., (*Archives of Physical Medicine and Rehabilitation* 52, 193 (1971)), clinically studied the administration of $H_6CoQ_4$ in the muscular dystrophies and in myotonia dystrophica, but no clinical benefit was observed in the human psudohypertrophic muscular dystrophy. Sovik, O., Stromme, J., Folkers, K., (*Acta. Paediat. Scand.* 60, 428 (1971)), administered $H_6CoQ_4$ to four cases of Duchenne muscular dystrophy. No improvement in muscular strength was observed, but there was a statistically significant decrease of CPK and aldolase for one boy. Danowski, T. S., Folkers, K., Wissinger, H. A., Hohmann, T. C., Gerneth, J. A., and Vester, J. W., (*Journal of Pharm. Sciences* 60, 640 (1971)) investigated the administration of $H_6CoQ_4$ to 19 boys with pseudohypertrophic muscular dystrophy of the Duchenne type. A battery of clinical and laboratory indices were monitored. No beneficial change was observed. The failure of $H_6CoQ_4$ to elicit a clinical effect in humans, but to do so in mice, might be partly explained by biochemical data that showed $H_6CoQ_4$ has only about 10-15% of the activity of $CoQ_{10}$ for DPNH-oxidase; (Lenaz, G., Daves, G. D., Folkers, K., *Arch. Biochem. Biophys.* 123, 539 (1968)), by dosage, species difference and protocol. Folkers, K., Littarru, G. P., Nakamura, R., and Scholler, J., (*Internat. J. Vit. Nutr. Res.* 42, 139 (1972)) used new enzyme methodology on muscle biopsies of dystrophic patients, and found that the succinate dehydrogenase-coenzyme $Q_{10}$ reductase was inactive for some patients and poorly active for others, which might result in no or poor response to treatment with CoQ. However, administration of CoQ and placebo appropriately reduced CPK. They emphasized the desirability of treatment with CoQ of pre-clinical stages of dystrophy, and Folkers, K., Nakamura, Littarru, G. P., Zellweger, H., Brunkhorst, J. B., Williams, C. Y., Langston, J. H., (*Proc. Nat'l. Acad. Sci.* 71(5), 2098–2102 (1974)) did administer $H_6CoQ_4$ and $CoQ_7$ to children with pre-clinical dystrophy. Extensive monitoring of enzyme levels revealed significant reductions of CPK. Couch, J. R., and Folkers, K., (*Biomedical and Clinical Aspects of Coenzyme Q,* Vol. 3, K. Folkers and Y. Yamamura, eds., Elsevier/North Holland Biomedical Press, Amsterdam, 257–266, (1981)) administrated $CoQ_{10}$ to two adults with limb-girdle dystrophy, and recorded a transient small improvement in strength, which appeared to slow deterioration. Folkers, K., Baker, L., Richardson, P. C., Shizukuishi, S., Takemura, K., Drzewoski, J., Lewandowski, J., Ellis, J., (*Biomedical and Clinical Aspects of Coenzyme Q,* Vol. 3, K. Folkers and Y. Yamamura, eds., Elsevier/North Holland Biomedical Press, Amsterdam, 399–412 (1981)) reported the administration of $CoQ_{10}$ to an adult with a late onset form of muscle disease for six years, and the expected deterioration of physical competence was markedly retarded.

Association of Muscular Disease with Cardiac Disease.

Welsh, J. D., Lynn, T. N., Haase, G. R., (*Archives of Internal Medicine* 112, 199–206 (1963)) reported upon the cardiac findings in 73 patients with muscular dystrophy, including the Duchenne, the limb-girdle, and the facioscapulohumeral forms, and patients with dystrophia myotonica. Zellweger, H., Durnin, R., Simpson, J., (*Acta. Neurol. Scandinav.* 48, 87 (1972)) evaluated the electrocardiograms for various muscular dystrophies. Kuhn, E., Fiehn, W., Schroder, J. M., Assmus, H., and Wagner, A., (*Neurology* 29, 1144–1149 (1979)) described the early myocardial disease of the Becker muscular dystrophy. Reeves, W. C., Griggs, R., Nanda, N. C., Thomson, K., Gramiak, R., (*Arch. Neurol.* 37, 273–277 (1980)) evaluated echocardiographic abnormalities in 24 subjects with Duchenne's dystrophy and 29 with myotonic muscular dystrophy. A significant incidence of cardiac abnormalities were demonstrable by echocardiography. Hopkins, L. C., Jackson, J. A., Elsas, L. J., (*Ann. Neurol.* 10, 230–237 (1981)) found that Emery/Dreifuss humeroperoneal muscular dystrophy may be associated with a potentially lethal cardiac arrhythmia. Goldberg. S. J., Stern, L. Z., Feldman, L., Allen, H. D., Sahn, D. J., Valdes-Cruz, L. M., (*Neurology* 32, 1101–1105 (1982)), by a computerized study, found ventricular abnormalities as Duchenne patients develop severe cardiac disease. Hawley, R. J., Gottdiener, J. S., Gay, J. A., Engel, W. K., (*Arch. Intern. Med.* 143, 2134–2136 (1983)) evaluated 30 patients with myotonic dystrophy and the incidence of substantial cardiac involvement. Durnin, R. E., Ziska, J., Chandramouli, B., (Journal of Iowa Medical Society, (1969)), found that 80% of 52 patients with progressive muscular dystrophy had abnormal electrocardiograms.

The association of cardiac disease with muscular disease is established.

Mitochondrial Myopathies.

Carafoli, E., Roman, I., (*Molecular Aspects of Medicine* 3, 295 (1980)) and Morgan-Hughes, J. A., (*Advanced Medicine* 19, K. B. Saunders, ed., Pitman Publishers Ltd., London, 243–260 (1983)), identified deficiencies of the mitochondrial respiratory chain or its associated phosphorylation system in muscle mitochondria from myopathies in man. Since $CoQ_{10}$ is an established constituent of the mitochondrial respiratory chain, these studies are basic to elucidation of human muscle disease.

Morgan-Hughes, J. A., Hayes, D. J., Clark, J. B., Cooper, J. M., (*Biomedical and Clinical Aspects of Coenzyme Q,* Vol. 4, K. Folkers and Y. Yamamura, eds., Elsevier/North Holland Biomedical Press, Amsterdam, 417–424 (1984)) conducted a most important study on isolated muscle mitochondria from 18 patients with myopathies. The respiratory activity, cytochrome content, and activities of several citric acid cycle enzymes were measured. The purity and integrity of the mitochondrial samples were documented. In ten cases of myopathy, the defect was in the first respiratory complex. In five cases, the deficiency was localized to the coenzyme Q-cytochrome $bc_1$ reductase complex. Respiratory rates were either low or not demonstrable with NAD-linked substrates or with succinate. Complex III deficiency was also monitored.

Measurement of Cardiac Function of Patients with Muscle Disease

All of the background research on the detection and some measurement of impaired cardiac function in patients with muscular disease only demonstrated an association of cardiac disease with muscular disease. Not one of those past studies involved the testing of anything to improve an impaired cardiac function. The conventional methods (echo cardiography, etc.) in cardiology of measuring cardiac function are essentially qualitative procedures useful for confirmation of diagnosis. These procedures are not sufficiently reliable and quantitative to monitor accurately over months of time cardiac function to determine whether the administration of any therapeutic agent is or is not effectively benefiting cardiac function.

Impedance cardiography offers a noninvasive, reproducible and acceptably quantitative measurement to monitor cardiac function over months of time. This technique has been described by Kubicek, W. G., Karnegis, J. N., Patterson, R. P., Witsoe, D. A. and Mattson, K. H., (*Aerospace Med.* 37, 1208–1212, 1966)). Therefore, impedance cardiography is the instrumentation of choice to monitor cardiac function of patients with muscle disease over months of time as coenzyme $Q_{10}$ is orally administered.

General Method (The First Double Blind Trial)

The selected patients, as volunteers, were monitored by four to six impedance cardiographic measurements during a 30 to 75-day control period. The instrument consisted of a cardiograph, a computer and a printer purchased from Surcom, Inc., 4180 Edmond Blvd., Minneapolis, Minn. 55406. The double-blind treatment was with daily capsules of $CoQ_{10}$ (33 mg $CoQ_{10}$/capsule, t.i.d.) and a matching placebo. Stroke volume, cardiac output and heart rate were monitored for a minimum of three measurements/month during of each month of a three-month period. Multiple measurements allowed statistical calculations. When there was a sustained clinical response judged by the cardiac output and or in the stroke volume, with statistical significance of $p<0.01$–$p<0.001$ during a three-month period, a blind assignment of $CoQ_{10}$ was made. When cardiac output and stroke volume had not significantly changed, not even by $p<0.05$ during a blind treatment period of three months, placebo was assigned, and the patients were then provided with open $CoQ_{10}$ on a crossover basis.

The blood levels of $CoQ_{10}$ were determined essentially by the method of Kishi, T., Okamoto, T., Kanamori, N., Yamagami, T., Kishi, H., Okada, A.., and Folkers, K., (*Biomedical and Clinical Aspects of Coenzyme Q*, Vol. 3, K. Folkers and Y. Yamamura, eds., Elsevier/North Holland Biomedical Press, Amsterdam, 67–78 (1981)), during the control and the blind periods of treatment. These data from the blind treatment period were not made available until after assignments of the patients to treatment with $CoQ_{10}$ or placebo were made, because knowledge of blood data prior to the blind assignments would have allowed assignments on the basis of blood data alone.

Results of the First Double Blind Trial

Blood Levels of $CoQ_{10}$. The control blood levels of $CoQ_{10}$ ranged from 0.50–0.84, which are lower than a mean plasma (only) level of $0.79\pm0.23$ $\mu$g/ml of presumably normal subjects; Kishi, et al., 1981 (31). These differences between levels in muscle disease and normal may be numerically small, but bioenergetically high. After oral $CoQ_{10}$, the increased blood levels ranged from 1.11–2.93 $\mu$g/ml.

Cardiac Function (Objective). Table I contains the data on the cardiac function of the patients during the double-blind trial with capsules of $CoQ_{10}$ and a matching placebo, and the crossover from blind placebo to open $CoQ_{10}$ at the time of assignment and decoding. Table II contains the data on assignments, code and $CoQ_{10}$-blood levels.

For a total of 12 patients, seven had progressive muscular dystrophies including the Duchenne, Becker, and limb-girdle dystrophies and five had neurogenic atrophies including the Charcot-Marie Tooth disease, and the Wohlfart-Kugelberg Welander disease.

Before decoding and the availability of the blood data, eight of the twelve patients were assigned $CoQ_{10}$ and the remaining four were assigned placebo. Decoding revealed that not one mistake of assignment had been made, $p<0.003$.

The patients who initially received blind $CoQ_{10}$ had the Duchenne and Becker dystrophies and Welander's disease and the patients initially receiving blind placebo had the limb-girdle and myotonic dystrophies and Charcot-Marie Tooth disease. All four patients initially receiving blind placebo were then treated for 3 months with open $CoQ_{10}$, and ¾ showed statistically significant increases in cardiac function.

Of the eight patients who were first treated with blind $CoQ_{10}$, two resigned from the study before the crossover period. Five of the six who were first treated with blind $CoQ_{10}$ maintained improved cardiac function during crossover with open $CoQ_{10}$, and one of these five, L. R., with Duchenne dystropy, age 7, responded better ($p<0.001$) in the 4th–6th month on $CoQ_{10}$ than in months 1–3 ($p<0.054$ for S. V.). The one patient, H. M. K. with Charcot-Marie Tooth disease, 63 years, relapsed to the impaired control level of cardiac function on placebo, after significant response, $p<0.001$, to blind $CoQ_{10}$. The control stroke volume of all 12 patients ranged from 29 to 100 ml./beat, but even the one patient (Becker's dystrophy) with a stroke volume of $100\pm16$ increased to $130\pm9$ ($p<0.001$) during $CoQ_{10}$ treatment. Stroke volume, in ml. of blood pumped/heart beat, is appraised as a prime criterion because it is independent of the heart rate, and impedance cardiography is superior in allowing beat-by-beat data. The cardiac outputs for all 12 subjects ranged from 3.1 to 7.2 L/min. The subject with CO of $7.2\pm1.6$ (Becker's dystrophy) increased to $9.0\pm0.4$ ($p<0.001$) on $CoQ_{10}$.

Introduction to Second Double Blind Trial

Coenzyme $Q_{10}$ ($CoQ_{10}$) is essential in the bioenergetics of the human cell and is one of the factors that sustains muscle activity. $CoQ_{10}$ is lipid-soluble and is present in the mitochondrial membrane and is an intermediate between NADH and succinate dehydrogenase and cytochrome b in the respiratory chain of human muscle tissue. (1,2). Folkers et al. (3) and Kamikawa et al. (4) have documented that coenzyme $Q_{10}$ is essential in the maintenance of normal heart function by regulating the energy metabolism in the myocardium. Diseases of the human heart are often correlated with a decrease in the levels of myocardial $CoQ_{10}$ (5,6). Many investigators have reported the association of cardiac disease with muscular disease (7, 8, 9, 10, 11, 12, 13, 14). Our first double blind study (15) showed the impaired myocardial function of patients with muscular dystrophy improved on $CoQ_{10}$ therapy, and there was also observed improved physical performance. The aim of this present study was to extend and to confirm our initial double blind trial on the administration of coenzyme $Q_{10}$ to patients with muscular dystrophy.

General Method (Second Double Blind Trial)

Fifteen muscular dystrophy patients (Table III), as volunteers, were monitored by four to six impedance cardiographic measurements during 14 to 96-day control periods. Cardiac performance was determined as stroke volume (SV) and cardiac output (CO) and was recorded at rest (16). The impedance cardiography provides a noninvasive, reproducible and acceptably quantitative measurement and is known to correlate with angiographic, dilution or ultrasound procedures to measure cardiac function (17, 18). The double blind treatment was with daily capsules of $CoQ_{10}$ (33 mg of $CoQ_{10}$ per capsules, t.i.d.) and a matching placebo. Heart rate, SV and CO were monitored for a minimum of three measurements per month during each month of the investigation period. Multiple measurements allowed statistical calculations. A sustained clinical response, judged by the cardiac output and/or the stroke volume with statistical significance of $p<0.01$ to $p<0.001$ during observation in the blind period allowed an assignment of $CoQ_{10}$ to be made. When cardiac output and stroke volume had not significantly changed during the blind treatment period, placebo was assigned, and the patients were then provided with open $CoQ_{10}$ on a crossover basis. Patient 8 with Becker's M. D. was a male, 14 years, who was obviously growing, and showed a modest increase in cardiac function on placebo and a greater increase on $CoQ_{10}$.

The blood levels of $CoQ_{10}$ were determined (19) during the control and blind periods of treatment. Blood data during treatment were not made available until after assignments of the patients to treatment with $CoQ_{10}$ or to placebo were made, because knowledge of blood data prior to the blind assignments would have allowed assignments on the basis of blood data alone. Statistic comparison of results were obtained using the Student-t test.

Results of the Second Double Blind Trial

The cardiac function of all 8 patients treated with $CoQ_{10}$ during double blind and all 7 placebo patients during crossover improved significantly (Table III). The cardiac performance of 6 patients on blind placebo did not significantly improve.

Of the 15 patients, 8 had cardiac functions at rest which were lower than the low value of a normal range (20). Four (having limb-girdle, Becker's and Charcot-Marie Tooth diseases) of these 8 had cardiac functions on therapy which were restored to a normal range. However, each of the 15 patients had a significantly improved cardiac function on therapy.

Patient #8, a fourteen year-old boy with Becker's muscular dystrophy, improved somewhat by SV and CO in the blind placebo period, but improved far more during crossover on $CoQ_{10}$. His improved cardiac performance in the placebo period was apparently caused by his markedly increased growth. His degree of growth was the basis of assignment of placebo. Two children (patients #1 and #15) did not show any marked body growth during the time of the study.

All assignments of the patients to treatment with $CoQ_{10}$ or placebo were made correctly (Table IV). The control blood levels of $CoQ_{10}$ ranged from 0.58 to 1.17 $\mu g/ml$ and increased more than two-fold during the $CoQ_{10}$ treatment period (Table II). Compliance is difficult to know, and it is doubtful that all patients had perfect compliance, which would relate to the blood levels of $CoQ_{10}$.

Our first double blind trial (15) was conducted with 12 patients, and this second trial was with 15 patients. Not a single mistake was made in assignment of treatment with $CoQ_{10}$ or placebo during the two double blind trials with a total of 27 patients with diverse muscular dystrophies.

Cardiac Performance. Muscular dystrophies are generally regarded as involving genetic defects and as incurable diseases. However, therapeutic benefit is possible for the sequelae of the genetic defects.

Cardiac involvement in the form of cardiomyopathy is a well known essential feature of muscular dystrophies. Ultrastructural studies have demonstrated that cardiac changes are similar to those detected in the "dystrophic" skeletal muscle (8, 9). The diagnosis of cardiac involvement was also based on the demonstration of typical electrocardiographic changes, namely tall R waves in $V_1$, with R/S ratio >1, and deep and narrow Q-waves in limb leads and over the left lateral precordium. Physical and radiographic examination of the heart appears less specific, because of the frequent presence of thoracic deformities and high diaphragms. In recent years, echocardiography has gained increasing recognition, also in the preclinical state, in the noninvasive assessment of functional and anatomic cardiac changes. In the present study, we have used impedance cardiography to evaluate cardiac performance. Impedance cardiography is a noninvasive, reproducible and is a quantitative measurement to monitor cardiac function over months of time. This technique has superiorities, as evaluated by Baker and Mistry (21), in comparison with other techniques to measure cardiac function in the study of $CoQ_{10}$ and dystrophy.

Mitochondrial Myopathies. Over the past decade, there have been many studies on the treatment of different cardiac diseases with $CoQ_{10}$ (22, 23, 24, 25, 26, 27). Carafoli et al. (28) and Morgan-Hughes et al. (29, 30) identified deficiencies in the mitochondrial respiratory chain or its associated phosphorylation system, in muscle mitochondria from myopathies in man. In 1986, Sholte et al. (31) found that the most frequently discovered defects in human mitochondria of patients with muscular disease are multiple defects in oxidative phosphorylation, NADH-CoQ reductase, $CoQ_{10}$-cytochrome $bc_1$, cytochrome $aa_3$, multiple respiratory chain defects, loose coupling and adenine nucleotide translocase. The rationale of this trial was based on known myocardial myopathies which involved respiratory enzymes, the known presence of $CoQ_{10}$ in respiration, and prior clinical data on $CoQ_{10}$ and dystrophy. The results show improved cardiac function by double blind $CoQ_{10}$ therapy for these dystrophic patients and are identical to the results of the prior study (15).

Conclusion. Therapy with $CoQ_{10}$ is oral, without any side effect, and may be administered for the lifetime of such patients with muscular dystrophy. At present, there is no therapy for such patients. The improved cardiac performance of such patients is apparently established.

REFERENCES FOR THE SECOND DOUBLE BLIND TRAIL WHICH ARE INCORPORATED BY REFERENCES HEREIN FOR REASONS STATED EARLIER

1. Crane, F. S., Hatefi, Y., Lester, R. L., Widmer, C., *Biochem. Biophys. Acta.* 25, 220–221 (1957).
2. De Pierre, J. W., Ernster, L., *Ann. Rev. Biochem.* 46, 201–262 (1977).
3. Folkers, K., Watanabe, T., Kaji, M., *J. Mol. Med.* 2, 431–460 (1977).
4. Kamikawa, T., Kobayashi, A., Yamashita, T., Hayashi, H., Yamazaki, N., *Am. J. Cardiol.* 56, 247–251 (1985).

5. Folkers, K., Littarru, G. P., Ho, L., Runge, T. H. M., Inter. *J. Vitamin. Nutr. Res.* 40, 380–390 (1970).
6. Mortensen, S. A., Vadhanavikit, S., Folkers, K., *Drugs Exptl. Res.* 10, 497–502 (1984).
7. Welsh, J. D., Lynn, T. N., Haase, G. F., *Arch. Intern. Med.* 112, 199–206 (1963).
8. Venco, A., Grandi, A., Barzizza F., Malamani, G., Ghisoni, A., Basano, D., *Neuropsychiatr. Eta. Evol.* 4(1), 61–66 (1984).
9. Kuhn, E., Fiehn, W., Schroder, J. M., Assmus, H., Wagner, A., *Neurology* 29, 1144–1149 (1979).
10. Carstens, V., Behrenbeck, D. S., *Herz Kreisl* 17, 147–153 (1985).
11. Hopkins, L. C., Jackson, J. A., Elsas, L. J., *Ann. Neurol.* 10, 230–237 (81981).
12. Goldberg, S. J., Stern, L. Z., Feldman, L., Allen, H. D., Sahn, D. J., Valdes-Cruz, L. M., *Neurology* 32, 1101–1105 (1982).
13. Hawley, R. J., Gottdiener, J. S., Gay, J. A., Engel, W. K., *Arch. Intern. Med.* 143, 2134–2136 (1983).
14. Saviotti, M., Casazza, F., Fiorista, F., Murpurgo, M., *Neuropsychiatr. Eta. Evol.* 4(1), 67–69 (1984).
15. Folkers, K., Wolaniuk, J., Simonsen, R., Morishita, M., Vadhanavikit, S., *Proc. Natl. Acad. Sci. USA* 82, 4513–4516 (1985).
16. Kubicek, W. G., Karnegis, J. N., Patterson, P. R., Witsoe, D. A., Mattson, R. H., *Aerospace Med.* 37, 1208–1212 (1966).
17. Edmunds, A. T., Godfrey, S., Tooley, M., *Clin. Sci.* 63, 107–113 (1982). 18. Veigl, V. L., Judy, W. V., *Cardiovas. Res.* 17, 728–734 (1983).
19. Vadhanavikit, S., Morishita, M., Duff, G. A., Folkers, K., *Biochem. Biophys. Res. Comm.* 123, 1165–1169 (1984).
20. Ganong, W. F., In: Review of Medical Physiology. Los Altos: Lange Medical Publication, 441–451 (1981).
21. Baker, L., Mistry, G. D., In: Biomedical and Clinical Aspects of Coenzyme Q, Vol. 3, K. Folkers and Y. Yamamura, eds., Amsterdam: Elsevier/North Holland Biomedical Press, 193–206 (1981).
22. Biomedical and Clinical Aspects of Coenzyme Q, Vol. 1. K. Folkers and Y. Yamamura, eds. Amsterdam: Elsevier/North Holland Biomedical Press (1977).
23. Biomedical and Clinical Aspects of Coenzyme Q, Vol. 2. K. Folkers, Y. Yamamura, and Y. Ito, eds. Amsterdam: Elsevier/North Holland Biomedical Press (1979).
24. Biomedical and Clinical Aspects of Coenzyme Q, Vol. 3. K. Folkers and Y. Yamamura, eds. Amsterdam: Elsevier/North Holland Biomedical Press (1981).
25. Biomedical and Clinical Aspects of Coenzyme Q, Vol. 4. K. Folkers and Y. Yamamura, eds. Amsterdam: Elsevier/North Holland Biomedical Press (1984).
26. Biomedical and Clinical Aspects of Coenzyme Q, Vol. 5. K. Folkers and Y. Yamamura, eds. Amsterdam: Elsevier/North Holland Biomedical Press (1986).
27. Coenzyme Q. G. Lenaz, ed. New York: John Wiley and Sons Ltd. (1985).
28. Carafoli, E., Roman, I., *Molecular Aspects of Medicine* 3, 295 (1980).
29. Morgan-Hughes, J. A., In: Advanced Medicine, Vol. 19, K. B. Saunders, ed., London: Pitman Publishers Ltd., 243–260 (1983).
30. Morgan-Hughes, J. A., Hayes, D. J., Clark, J. B., Cooper, J. M., Biomedical and Clinical Aspects of Coenzyme Q, K. Folkers and Y. Yamamura, eds., Elsevier/North Holland Biomedical Press, Amsterdam, 417–424 (1984).
31. Sholte, H. R., Luyt-Houwen, I. E. M., Busch, H. F. M., Vaandragen-Verduin. New York Academy of Sciences, Como meeting (May, 1986).

TABLE I

Data on Cardiac Function of Patients

| Patient Sex, Age | Diagnosis | Treatment* Duration, (days) C* | B* | O* | | C, Control | B, Double Blind | | O, Open | |
|---|---|---|---|---|---|---|---|---|---|---|
| | | | | | | | Functional Data; Mean ± S.D. a, Cardiac Output (CO), L/min. b, Stroke Volume (SV), ml. c, Heart Rate (HR), beats/min. | | | |
| 1. M. B. F 45 | Limb-Girdle Dystrophy | 48 | 60 | 300 | a, | 5.2 ± 0.3 | 5.0 ± 0.6 | n.s. | 6.4 ± 0.4 | $p < 0.001$ |
| | | | | | b, | 57 ± 7 | 60 ± 1 | n.s. | 69 ± 4 | $p < 0.001$ |
| | | | | | c, | 96 ± 8 | 84 ± 11 | — | 98 ± 3 | — |
| 2 L. R. M 7 | Duchenne Dystrophy | 75 | 70 | 270 | a, | 3.1 ± 0.4 | 3.4 ± 0.2 | n.s. | 4.0 ± 0.1 | $p < 0.001$ |
| | | | | | b, | 30 ± 5 | 34 ± 7 | $p < 0.5$ | 37 ± 8 | $p < 0.001$ |
| | | | | | c, | 102 ± 8 | 101 ± 9 | — | 107 ± 7 | — |
| 3 D. M. M 16 | Myotonic Dystrophy | 50 | 61 | 180 | a, | 3.3 ± 0.4 | 3.4 ± 0.2 | n.s. | 4.2 ± 0.5 | $p < 0.001$ |
| | | | | | b, | 29 ± 4 | 30 ± 1 | n.s. | 42 ± 8 | $p < 0.001$ |
| | | | | | c, | 118 ± 6 | 110 ± 2 | — | 101 ± 10 | — |
| 4 K. A. C. M 7 | Duchenne Dystrophy | 29 | 113 | 172 | a, | 4.2 ± 0.6 | 5.2 ± 0.2 | $p < 0.001$ | 4.5 ± 0.7 | $p < 0.001$ |
| | | | | | b, | 38 ± 6 | 48 ± 3 | $p < 0.001$ | 42 ± 8 | $p < 0.001$ |
| | | | | | c, | 108 ± 3 | 107 ± 8 | — | 107 ± 4 | — |
| 5. H. L. D. F 39 | Limb-Girdle Dystrophy | 37 | 122 | 110 | a, | 6.0 ± 0.5 | 5.7 ± 0.4 | n.s. | 5.5 ± 0.3 | n.s. |
| | | | | | b, | 79 ± 7 | 72 ± 2 | n.s. | 73 ± | n.s. |
| | | | | | c, | 77 ± 3 | 76 ± 6 | — | 75 ± | — |
| 6. J. L. J. M 25 | Becker's Dystrophy | 29 | 180 | | a, | 7.2 ± 1.6 | 9.0 ± 0.4 | $p < 0.001$ | D | |
| | | | | | b, | 100 ± 16 | 130 ± 9 | $p < 0.001$ | D | |
| | | | | | c, | 69 ± 4 | 71 ± 4 | — | | |
| 7. D. L. K. M 37 | Becker's Dystrophy | 60 | 150 | | a, | 5.9 ± 1.1 | 6.9 ± 1.0 | $p < 0.001$ | 7.42 ± 1.36 | $p < 0.001$ |
| | | | | | b, | 80 ± 12 | 99 ± 16 | $p < 0.001$ | 106 ± 26.63 | $p < 0.01$ |
| | | | | | c, | 76 ± 6 | 68 ± 4 | — | 70 | — |
| 8. W. P. F 69 | Charcot-Marie Tooth Disease | 28 | 121 | 90 | a, | 5.2 ± 0.2 | 5.7 ± 0.2 | n.s. | 6.3 ± 0.8 | $p < 0.001$ |
| | | | | | b, | 67 ± 6 | 69 ± 2 | n.s. | 85 ± 12 | $p < 0.001$ |
| | | | | | c, | 77 ± 3 | 76 ± 3 | — | 74 ± 2 | — |
| 9. H. M. K. F 63 | Charcot-Marie Tooth Disease | 32 | 91 | 96 | a, | 5.3 ± 0.8 | 6.5 ± 1.1 | $p < 0.001$ | 4.6 ± 0.4 | n.s. E |
| | | | | | b, | 71 ± 9 | 89 ± 13 | $p < 0.001$ | 67 ± 2 | n.s. E |
| | | | | | c, | 73 ± 4 | 73 ± 2 | — | 71 ± 6 | — |

TABLE I-continued

Data on Cardiac Function of Patients

Functional Data; Mean ± S.D.
a, Cardiac Output (CO), L/min.
b, Stroke Volume (SV), ml.
c, Heart Rate (HR), beats/min.

| Patient Sex, Age | Diagnosis | Treatment* Duration, (days) C* | B* | O* | | C, Control | B, Double Blind | | O, Open | |
|---|---|---|---|---|---|---|---|---|---|---|
| 10. B. H. M 31 | Charcot-Marie Tooth Disease | 30 | 105 | | a, b, c, | 4.0 ± 0.4 61 ± 8 67 ± 4 | 4.2 ± 0.6 70 ± 11 60 ± 6 | n.s. p < 0.001 — | D D — | |
| 11. M. D. F 63 | Charcot-Marie Tooth Disease | 45 | 90 | 300 | a, b, c, | 5.0 ± 0.3 68 ± 8 74 ± 6 | 5.3 ± 0.2 76 ± 5 70 ± 3 | n.s. p < 0.001 n.s. | 6.3 ± 0.6 83 ± 5 75 ± 4 | p < 0.001 p < 0.001 — |
| 12. C.S. F 49 | Welander Disease | 43 | 120 | 180 | a, b, c, | 3.9 ± 0.5 68 ± 6 57 ± 6 | 4.5 ± 0.5 84 ± 9 54 ± 5 | p < 0.001 p < 0.001 — | 4.6 ± 0.5 74 ± 11 62 ± 5 | p < 0.001 p < 0.001 — |

*C = Control,
B = Blind, coded period of study,
O = Open period of study
D = Resigned from study
E = Crossover placebo period

TABLE II

Double Blind and Open Trial Data and Blood Data

| Patient Sex, Age | Double Blind Assignment | Code | $CoQ_{10}$ Blood Levels Average μg/ml Control | Blind | Open |
|---|---|---|---|---|---|
| 1. M. B.; F 45 | Placebo | Placebo | 0.63 | 0.61 | 1.40; $CoQ_{10}$ |
| 2. L. R.; M 7 | $CoQ_{10}$ | $CoQ_{10}$ | 0.62 | 1.11 | 1.24; $CoQ_{10}$ |
| 3. D. M.; M 16 | Placebo | Placebo | 0.58 | 0.61 | 1.32; $CoQ_{10}$ |
| 4. K. A. C.; M 7 | $CoQ_{10}$ | $CoQ_{10}$ | 0.50 | 1.94 | 1.47; $CoQ_{10}$ |
| 5. H. L. D.; F 39 | Placebo | Placebo | 0.68 | 0.63 | 1.76; $CoQ_{10}$ |
| 6. J. L. J.; M 25 | $CoQ_{10}$ | $CoQ_{10}$ | 0.71 | 1.22 | — |
| 7. D. L. K.; M 37 | $CoQ_{10}$ | $CoQ_{10}$ | 0.55 | 1.16 | 1.13; $CoQ_{10}$ |
| 8. W. P.; M 69 | Placebo | Placebo | 0.84 | 0.77 | 2.13; $CoQ_{10}$ |
| 9. H. M. K.; F 63 | $CoQ_{10}$ | $CoQ_{10}$ | 0.82 | 2.93 | 1.12; P |
| 10. B. H.; M 31 | $CoQ_{10}$ | $CoQ_{10}$ | 0.59 | 2.09 | — |
| 11. M. D.; F 63 | $CoQ_{10}$ | $CoQ_{10}$ | 0.68 | 1.96 | 1.43; $CoQ_{10}$ |
| 12. C. S.; F 49 | $CoQ_{10}$ | $CoQ_{10}$ | 0.78 | 1.58 | 2.03; $CoQ_{10}$ |

TABLE III

MUSCULAR DYSTROPHY PATIENTS
DETAILS OF DATA ON CARDIAC FUNCTION

Functional Data; Mean ± S.D.
A. Cardiac Output (CO), L/min
B. Stroke Volume (SV) ml/beat
C. Heart Rate (HR) beats/min

| No. | Patient, Sex, Age | Diagnosis | Treatment (Days) Ctrl[a] | DB[b] | O[c] | Control[a] | | Double Blind[b] | | | Open[c] $Q_{10}$, crossover. | |
|---|---|---|---|---|---|---|---|---|---|---|---|---|
| 1. | J. A. (M,8) | Duchenne M.D. | 96 | 105 | 182 | A. B. C. | 5.3 ± 0.7 65 ± 9 80 ± 9 | A. B. C. | 5.6 ± 0.7 66 ± 16 86 ± 10 | n.s. n.s. — | A. B. C. | 6.6 ± 0.8 80 ± 7 87 ± 8 | p<0.001 p<0.001 — |
| 2. | J. P. B. (M,43) | Limb-girdle M.D. | 78 | 102 | 862 | A. B. C. | 5.3 ± 0.3 73 ± 5 77 ± 2 | A. B. C. | 5.5 ± 0.3 75 ± 5 73 ± 4 | n.s. n.s. — | A. B. C. | 5.8 ± 0.7 73 ± 10 79 ± 5 | p<0.001 n.s. — |
| 3. | D. C. (M,33) | Fascioscapulo-humeral M.D. | 30 | 186 | 69 | A. B. C. | 7.9 ± 0.7 129 ± 1 64 ± 4 | A. B. C. | 8.1 ± 1.4 132 ± 8 63 ± 10 | n.s. n.s. — | A. B. C. | 11.1 ± 1.4 168 ± 21 65 ± 7 | <0.001 p<0.001 — |
| 4. | D. H. (M,54) | Charcot-Marie-Tooth M.D. | 20 | 126 | 34 | A. B. C. | 7.9 ± 0.8 126 ± 14 62 ± 1 | A. B. C. | 8.1 ± 0.7 129 ± 10 61 ± 2 | n.s. n.s. — | A. B. C. | 11.8 ± 2.3 186 ± 31 78 ± 4 | p<0.001 p<0.001 — |
| 5. | P. K. (F,31) | Limb-girdle M.D. | 34 | 481 | 890 | A. B. C. | 4.5 ± 0.4 46 ± 9 99 ± 9 | A. B. C. | 5.4 ± 0.4 59 ± 7 91 ± 5 | p<0.001 p<0.001 — | A. B. C. | 6.2 ± 0.5 69 ± 4 89 ± 5 | p<0.001 p<0.001 — |
| 6. | M. R. (M,27) | Charcot-Marie-Tooth M.D. | 14 | 158 | 68 | A. B. C. | 9.1 ± 0.8 135 ± 17 68 ± 8 | A. B. C. | 12.2 ± 1.7 188 ± 14 64 ± 5 | p<0.001 p<0.001 — | A. B. C. | 11.9 ± 1.4 195 ± 11 62 ± 6 | p<0.001 p<0.001 — |
| 7. | M. R. (F,33) | Hypotonic congenitale | 24 | 118 | 260 | A. B. C. | 6.9 ± 0.6 82 ± 6 84 ± 7 | A. B. C. | 7.5 ± 0.1 95 ± 5 79 ± 5 | p<0.001 p<0.001 — | A. B. C. | 10.4 ± 2.1 124 ± 19 83 ± 6 | p<0.001 p<0.001 — |
| 8. | T. A. W. (M,14) | Becker's M.D. | 16 | 131 | 124 | A. B. C. | 6.1 ± 0.5 57.2 ± 11 104 ± 2 | A. B. C. | 7.3 ± 0.7 74 ± 7 99 ± 4 | p<0.001 p<0.001 — | A. B. C. | 9.7 ± 1.7 97 ± 15 99 ± 3 | p<0.001 p<0.001 — |
| 9. | J. M. (F,58) | Charcot-Marie-Tooth M.D. | 30 | 120 | 359 | A. B. C. | 5.0 ± 0.9 60 ± 9 84 ± 2 | A. B. C. | 5.5 ± 0.9 57 ± 9 98 ± 6 | n.s. n.s. — | A. B. C. | 6.6 ± 1.7 70 ± 16 93 ± 5 | p<0.001 p<0.001 — |
| 10. | T. D. (M,31) | Limb-girdle M.D. | 21 | 66 | 667 | A. B. | 3.8 ± 0.3 46 ± 4 | A. B. | 4.8 ± 0.7 68 ± 5 | p<0.001 p<0.001 | A. B. | 5.6 ± 0.5 72 ± 6 | p<0.001 p<0.001 |

TABLE III-continued

MUSCULAR DYSTROPHY PATIENTS
DETAILS OF DATA ON CARDIAC FUNCTION

Functional Data; Mean ± S.D.
A. Cardiac Output (CO), L/min
B. Stroke Volume (SV) ml/beat
C. Heart Rate (HR) beats/min

| Patient, No. Sex, Age | Diagnosis | Treatment (Days) Ctrl[a] | DB[b] | O[c] | Control[a] | | Double Blind[b] | | Open[c] $Q_{10}$, crossover. | |
|---|---|---|---|---|---|---|---|---|---|---|
| 11. L. L. (M,38) | Myotonic M.D. | 27 | 172 | 539 | C. 83 ± 4<br>A. 3.0 ± 0.4<br>B. 50 ± 7 | | C. 72 ± 2<br>A. 3.4 ± 0.3<br>B. 60 ± 4 | —<br>n.s.<br>$p<0.01$ | C. 77 ± 2<br>A. 3.7 ± 0.4<br>B. 65 ± 5 | —<br>$p<0.01$<br>$p<0.001$ |
| 12. T. E. P. (M,74) | Limb-girdle M.D. | 19 | 120 | 721 | C. 61 ± 8<br>A. 2.7 ± 0.6<br>B. 41 ± 8 | | C. 58 ± 6<br>A. 3.4 ± 0.3<br>B. 52 ± 4 | —<br>$p<0.01$<br>$p<0.01$ | C. 57 ± 7<br>A. 3.3 ± 0.4<br>B. 51 ± 4 | —<br>$p<0.001$<br>$p<0.001$ |
| 13. M. T. (F,69) | Limb-girdle M.D. | 20 | 150 | 560 | C. 65 ± 2<br>A. 3.2 ± 0.5<br>B. 39 ± 6 | | C. 65 ± 5<br>A. 3.5 ± 0.3<br>B. 41 ± 4 | —<br>n.s.<br>n.s. | C. 69 ± 5<br>A. 4.9 ± 0.9<br>B. 56 ± 8 | —<br>$p<0.001$<br>$p<0.001$ |
| 14. B. H. (F,53) | Welander M.D. | 22 | 75 | 695 | C. 81 ± 3<br>A. 3.2 ± 0.5<br>B. 43 ± 4 | | C. 85 ± 6<br>A. 4.6 ± 0.4<br>B. 62 ± 3 | —<br>$p<0.001$<br>$p<0.001$ | C. 87 ± 6<br>A. 4.2 ± 0.3<br>B. 55 ± 8 | —<br>$p<0.001$<br>$p<0.001$ |
| 15. B. S. (M,15) | Becker's M.D. | 31 | 90 | 348 | C. 75 ± 6<br>A. 8.1 ± 1.2<br>B. 96 ± 11<br>C. 84 ± 5 | | C. 74 ± 7<br>A. 9.1 ± 1.5<br>B. 115 ± 8<br>C. 79 ± 9 | —<br>n.s.<br>$p<0.001$<br>— | C. 77 ± 7<br>A. 11.1 ± 2.5<br>B. 130 ± 27<br>C. 84 ± 6 | —<br>$p<0.001$<br>$p<0.001$<br>— |

[a]Control
[b]Double Blind, Coded Period of Study
[c]Open Period of Study

TABLE IV

RESULTS OF DOUBLE BLIND AND OPEN TRIAL
DATA AND BLOOD DATA

| Patient; No. Sex, Age | Double Blind Assignment | Code | $CoQ_{10}$ Blood Levels Average μg/ml Control | Blind | Crossover |
|---|---|---|---|---|---|
| 1. J. A.; M, 8 | Placebo | Placebo | 0.61 | 0.53 | 1.62 |
| 2. J. P. B.; M, 43 | Placebo | Placebo | 0.72 | 0.84 | 2.48 |
| 3. D. C.; M, 33 | Placebo | Placebo | 0.94 | 0.75 | 1.68 |
| 4. D. H.; M, 54 | Placebo | Placebo | 0.89 | 0.83 | 0.94 |
| 5. P. K.; F, 31 | $CoQ_{10}$ | $CoQ_{10}$ | 0.66 | 2.24 | 2.84 |
| 6. M. R.; M, 27 | $CoQ_{10}$ | $CoQ_{10}$ | 0.64 | 1.05 | 1.17 |
| 7. M. R.; F, 33 | $CoQ_{10}$ | $CoQ_{10}$ | 0.74 | 1.81 | 1.27 |
| 8. T. A. W.; M, 14 | Placebo | Placebo | 0.81 | 0.82 | 1.42 |
| 9. J. M.; F, 58 | Placebo | Placebo | 0.93 | 1.00 | 2.05 |
| 10. T. D.; M, 31 | $CoQ_{10}$ | $CoQ_{10}$ | 1.17 | 2.74 | 2.48 |
| 11. L. L.; M, 38 | $CoQ_{10}$ | $CoQ_{10}$ | 0.65 | 1.85 | 1.72 |
| 12. T. E. P.; M, 74 | $CoQ_{10}$ | $CoQ_{10}$ | 1.04 | 2.29 | 2.45 |
| 13. M. T.; F, 69 | Placebo | Placebo | 0.90 | 0.80 | 1.70 |
| 14. B. H.; F, 53 | $CoQ_{10}$ | $CoQ_{10}$ | 0.95 | 2.20 | 2.50 |
| 15. B. S.; M, 15 | $CoQ_{10}$ | $CoQ_{10}$ | 0.58 | 1.38 | 1.44 |
| Mean ± S.D. | | | 0.81 ± 0.17 | $p < 0.001$ | 1.85 ± 0.56 |

What is claimed:

1. A method for treating impaired cardiac function of human patients having the Duchenne dystrophy, the Becker dystrophy, the limb-girdle dystrophies, myotonic dystrophy, Charcot-Marie-Tooth disease fascioscapulohumoral muscular disease, hypotonia congenitale or Welander disease, or a closely related disease, said method comprising administering to the patients having any one of these dystrophies or myopathies a therapeutically effective amount of a formulation consisting essentially of coenzyme $Q_{10}$.

* * * * *